United States Patent [19]

Gelbein et al.

[11] 4,174,452

[45] Nov. 13, 1979

[54] PRODUCTION OF CARBOXYLIC ACIDS FROM NITRILES

[76] Inventors: Abraham P. Gelbein, 925 Woodland Ave., Plainfield, N.J. 07060; John E. Paustian, 38 Adams Dr., Whippany, N.J. 07981; Anthony J. Fanelli, 63 Upper Mountain Ave., Rockaway, N.J. 07866

[21] Appl. No.: 877,339

[22] Filed: Feb. 13, 1978

Related U.S. Application Data

[63] Continuation of Ser. No. 730,386, Oct. 7, 1976, abandoned.

[51] Int. Cl.$^2$ .................. C07D 213/55; C07C 63/26
[52] U.S. Cl. ................................. 546/319; 562/484; 562/490; 562/493

[58] Field of Search ............... 260/295.5 R, 515 R, 260/515 P; 562/493, 490, 484; 546/319

[56] References Cited

U.S. PATENT DOCUMENTS

| 3,285,956 | 11/1966 | Holsten et al. | 260/515 P |
| 3,492,345 | 1/1970 | Neugebauer et al. | 260/515 P |

Primary Examiner—Alan L. Rotman
Attorney, Agent, or Firm—Louis E. Marn; Elliot M. Olstein

[57] ABSTRACT

A nitrile, such as terephthalonitrile or nicotinonitrile is reacted with water, in the vapor phase, in the presence of a catalyst, such as supported phosphoric acid, to produce the corresponding carboxylic acid.

14 Claims, No Drawings

PRODUCTION OF CARBOXYLIC ACIDS FROM NITRILES

This is a continuation of application Ser. No. 730,386, filed Oct. 7, 1976, now abandoned.

This invention relates to the production of carboxylic acids, and more particularly to the production of carboxylic acids from nitriles.

Aromatic or heterocyclic nitriles are generally converted to the corresponding carboxylic acid by aqueous hydrolysis which is catalyzed by an acid or base. Thus, for example, terephthalonitrile has been hydrolyzed with aqueous ammonia to produce the corresponding ammonium salt, which is then converted to the acid by steam stripping. Although such hydrolysis reactions are capable of producing the acid from the nitrile, there is a need for improvements in the production of carboxylic acids from nitriles.

An object of this invention is to produce carboxylic acids.

A further object of this invention is to produce aromatic and heterocyclic carboxylic acids from the corresponding nitriles.

These and other objects of the present invention should be more apparent from reading the following detailed description thereof.

In accordance with the present invention, a nitrile and/or an intermediate hydrolysis product thereof is reacted with water, in the vapor phase, in the presence of a suitable catalyst to convert the nitrile and/or an intermediate hydrolysis product to the corresponding carboxylic acid.

The organic materials which are employed as starting materials for producing carboxylic acids in accordance with the present invention are either aromatic or heterocyclic nitriles. The aromatic nitriles contain one or more cyano-groups, preferably one or two cyano-groups and can be unsubstituted or substituted with other substituent groups; e.g., an alkyl group. The aromatic nucleus is preferably benzene or naphthalene. As representative examples, there may be mentioned; phthalonitrile, terephthalonitrile, isophthalonitrile, tolunitrile, 1-cyanonaphthalene, and 2,6-cyanonaphthalene. Similarly, the heterocyclic nitriles can contain one or more cyano-groups, with the heterocyclic nucleus generally being pyridine. The preferred starting materials are nicotinonitrile, isophthalonitrile, terephthalonitrile and phthalonitrile. As hereinabove noted, the starting material may be a nitrile intermediate hydrolysis product, such as the imides, amides, cyano-acids, cyano-amides, and amide-acids, which can be employed alone or in combination with each other or the nitrile starting material.

The catalyst employed for the vapor phase hydrolysis of the invention is a solid acid catalyst. As representative catalysts, there may be mentioned: silica gel, silica-alumina, supported phosphoric acid, Group III metal phosphates and sulfates, e.g., phosphates and sulfates of aluminum, boron and gallium, transition metal oxides; e.g., one or more oxides of vanadium, chromium, manganese, iron, cobalt, nickel, etc. The catalysts are of the type employed for hydration, dehydration and esterification reactions. The preferred catalyst is supported phosphoric acid.

The nitrile and water are reacted, in the vapor phase at temperatures which are generally of from 200° F. to 1,000° F., and preferably of from 400° F. to 800° F. The temperatures which are employed are generally above the dew point of both the feed and product components. The temperatures are most preferably selected to provide at least a 50% conversion of the nitrile at a contact or reaction time of no greater than one minute.

The water is employed in at least stoichiometric proportions; however, an excess of water is preferably employed in that reaction kinetics are more favorable at higher water partial pressures. The stoichiometric excess of water can be as much as to provide a water to nitrile mole ratio of up to 500:1 with the water to nitrile mole ratio generally being from 5:1 to 50:1. The use of an excess of water also functions to maintain vapor phase conditions; however, an inert gaseous diluent, such as nitrogen, can be used for such purposes.

The total reaction pressure is generally selected to provide the desired water partial pressure, with such total pressures generally being from 1 to 10 atm.

The catalytic vapor phase reaction may be effected by any one of a wide variety of reaction techniques, including fixed bed, fluidized bed, dilute phase transport, etc., and the selection of a specific technique is deemed to be within the scope of those skilled in the art from the present teachings.

The gaseous reaction effluent contains the carboxylic acid, unreacted starting nitrile, ammonia, and some reaction intermediates. Thus, for example, in the production of terephthalic acid from terephthalonitrile the gaseous reaction effluent includes terephthalic acid, ammonia, unreacted terephthalonitrile, reaction intermediates, such as cyanobenzoic acid, terephthalamic acid, terephthalamide, as well as any unreacted water. The reaction mixture can be cooled to condense the entire effluent and produce a water solution and slurry of the ammonium salts of terephthalic acid and intermediate hydrolysis products. The terephthalic acid and intermediate hydrolysis products can be separated from the ammonia by the addition of a suitable acid; for example, hydrochloric acid.

The separation may also be effected as described in concurrently filed U.S. application Ser. No., (730,385, filed Oct. 7, 1976) and assigned to the same assignee.

The invention will be described with reference to the following examples; however, the scope of the invention is not to be limited thereby.

EXAMPLE 1

A U-shaped, 1" O.D. stainless reactor, 40" total length, was charged with 200 grams of a pelleted 10% $H_3PC_4$ on silica-alumina catalyst. The reaction was heated to 250° C. in an air bath and a vaporized 1% ammonia solution passed over the catalyst for one hour, then flushed with nitrogen and heated to 300° C.

Terephthalonitrile was heated to 230° C. in a steel cylinder, through which nitrogen was passed at a rate of 1 liter/min. such that approximately 0.5 g of terephthalonitrile (TPN) per minute was volatilized and passed through heated tubing into the reactor. Water, at the rate of 1.3 g/min., was also vaporized and passed into the reactor co-currently with the TPN/nitrogen. The mole ratio $H_2O$/TPN was approximate 18.

The reactor effluent was condensed in an ice bath. The resulting product consisted of a white solid slurried in water. The mixture was acidified with hydrochloric acid to precipitate terephthalic acid (TPA) dissolved as the ammonium salt. The resulting solids were filtered, washed with water and analyzed by liquid chromatography. The solid consisted of a mixture of 58% unreacted TPN, 5% terephthalamic acid/cyanobenzoic acid and 37% terephthalic acid.

EXAMPLE 2

The system of Example 1 is operated at a temperature of 350° C. and a pressure of 35 psig. TPN is fed at a rate of 5 millimoles/min. and steam at the rate of 83 millimoles/min. The run was effected for a period of 50 minutes.

The product contained 45.7 wt.% TPA; 38.2 wt.% cyanobenzoic acid; 9 wt.% terephthalamic acid; and 7.1 wt.% TPN.

The present invention is particularly advantageous in that the nitrile is converted to the acid in shorter reaction times and at lower pressures than achieved with conventional liquid hydrolysis. In addition, less expensive materials of construction can be employed.

Numerous modifications and variations of the present invention are possible in light of the above teachings, and therefore, within the scope of the appended claims, the invention may be practiced otherwise than as particularly described.

What is claimed is:

1. In an acid catalyzed process for producing a carboxylic acid from a nitrile, the improvement comprising:
reacting water and a nitrile selected from the group consisting of (1) nicotinonitrile and intermediate hydrolysis products thereof, and (2) aromatic nitriles having at least one cyano group substituted on an aromatic nucleus selected from the group consisting of benzene and naphthalene and intermediate hydrolysis products thereof, in the vapor phase, in the presence of an acid catalyst in solid form, at a temperature of from 200° F. to 1,000° F., said temperature being above the dew point of the nitrile and corresponding carboxylic acid product to produce a gaseous effluent containing the corresponding carboxylic acid.

2. The process of claim 1 wherein the catalyst is selected from the group consisting of silica gel, silica-alumina, supported phosphoric acid, Group III metal phosphates, Group III metal sulfates and transition metal oxides.

3. The process of claim 2 wherein the catalyst is supported phosphoric acid.

4. The process of claim 1 wherein the catalyst is selected from the group consisting of silica gel, silica-alumina, supported phosphoric acid, Group III metal phosphates, Group III metal sulfates and transition metal oxides.

5. The process of claim 4 wherein the catalyst is supported phosphoric acid.

6. The process of claim 1 wherein said member is said aromatic nitrile.

7. The process of claim 6 wherein said member is selected from the group consisting of phthalonitrile, terephthalonitrile and isophthalonitrile.

8. The process of claim 2 wherein said reaction is effected at a temperature at which there is a 50% conversion of nitrile at a contact time of no greater than 1 minute.

9. The process of claim 1 wherein said member is nicotinonitrile.

10. The process of claim 2 wherein said member is terephthalonitrile.

11. The process of claim 7 wherein said vapor phase hydrolysis is effected with a stoichiometric excess of water to provide a water to nitrile mole ratio of up to 500 to 1.

12. The process of claim 9 wherein the vapor phase hydrolysis is effected with a stoichiometric excess of water to provide a water to nitrile mole ratio of up to 500 to 1.

13. The process of claim 7 wherein the temperature is from 400° F. to 800° F.

14. The process of claim 9 wherein the temperature is from 400° F. to 800° F.

* * * * *